US00PP15396P3

(12) United States Plant Patent
Twomey

(10) Patent No.: US PP15,396 P3
(45) Date of Patent: Dec. 7, 2004

(54) HYBRID TEA ROSE PLANT NAMED 'TWOAGAIN'

(50) Latin Name: *Rosa hybrida*
Varietal Denomination: Twoagain

(75) Inventor: Jerry F. Twomey, 194 Avocado St., Leucadia, CA (US) 92024

(73) Assignee: Jerry F. Twomey

( * ) Notice: Subject to any disclaimer, the term of this patent is extended or adjusted under 35 U.S.C. 154(b) by 253 days.

(21) Appl. No.: 10/035,286

(22) Filed: Jan. 3, 2002

(65) Prior Publication Data

US 2003/0126652 P1 Jul. 3, 2003

(51) Int. Cl.[7] ..... A01H 5/00

(52) U.S. Cl. ..... Plt./140

(58) Field of Search ..... Plt./140, 139, 151, Plt./150

*Primary Examiner*—Howard J. Locker

(57) ABSTRACT

A new rose cultivar of the Hybrid Tea class characterized by having two to three clusters at one time of large scarlet flowers, each cluster having 8 to 12 flowers, on a very vigorous healthy plant. This plant is marketed in the U.S. as: Dream Scarlet.

1 Drawing Sheet

1

The present invention relates to a new and distinctive cultivar of rose plant (*Rosa hybrida*) of the Hybrid Tea class, which was originated by my crossing 'Karma' as the seed parent with the pollen parent an unknown seedling.

Among the novel characteristics possessed by the new cultivar which distinguish it from:

(a) All other cultivars of which I am aware are: (1) Mature plants have 2–3 basal canes with clusters of 8–12 large flowers. (2) Flowers almost continously. (3) Scarlet, non-fading red flowers. (4) Tall vigorous healthy bush.

(b) Seed parent: Semi-double, medium red. Pollen parent: Unknown.

Asexual reproduction of the new rose cultivar by budding, as performed at Wasco, Calif., shows that the aforementioned and all other distinctive characteristics come true to form and are established and transmitted through succeeding propagations.

The accompanying drawing shows typical specimens of the vegetative growth and flowers of the new cultivar in different stages of development and as depicted in color as nearly true as it is reasonably possible to make the same in a color illustration of this character.

The following is a detailed description of my new cultivar, with color terminology in accordance with The Royal Horticultural Society Colour Chart (R.H.S.C.C.). The terminology used in the color description herein refers to plate numbers in the aforementioned color chart, e.g. "53A" is plate "53A" of The Royal Horticultural Society Colour Chart.

Parentage:

*Seed parent*.—'Karma' aka 'Pounder Star' (not patented).

*Pollen parent*.—Unknown.

Class: Hybrid Tea.

The following observations are made of specimens grown outdoors in Monterey County, Calif., in the month of September.

2

FLOWER

Blooming habit:

A. Bud:

(1) *Size*.—Sepals enclosed, 22–25 mm from base of sepals to top of bud.

(2) *Form*.—Ovoid.

(3) *Sepals*.—35–40 mm in length; 11–15 mm extension beyond bud; no serration shown on sepal edges. Generally 3 out of 5 sepals show appendages on each side, 4 to 9 mm length. Sepals show glandular development on edges and outer surface. Heavy cotton matting on inner surface, no matting on outer surface. Outside color — 144A with heavy shadings of 185D, inside — 194C.

(4) *Peduncle*.—Length 8–9 cm. Surface smooth with some glandular hairs. Strength — firm; Color — 148B with light shadings of 181B.

(5) *Receptacle*.—Oblong, 11–14 mm diameter. Color same as peduncle.

(6) *Color*.—When sepals first divide, outside bud petals near to 53A with blackish shadings.

B. Bloom:

(1) *Size*.—When open: 10–11 cm.

(2) *Borne*.—8 to 12 blooms on cluster.

(3) *Form*.—Globular.

(4) *Petalage*.—Average — 40 to 44.

(5) *Color*.—Early open: outer petals near 53B; base 155B; inner petals near 53A. Aging: Near 46A, base 155B.

C. Petals:

(1) *Texture*.—Firm.

(2) *Appearance*.—Satiny.

(3) *Form*.—Rounded smooth edge.

(4) *Arrangement*.—Regular.

(5) *Petaloids in center*.—Average 9–11.

(6) *Persistence*.—Heavy substance, long lasting.

(7) *Fragrance*.—Mild, distinct.

(8) *Lasting quality*.—On plant 14–16 days; cut 10–12 days.

REPRODUCTIVE ORGANS

A. Stamen:
(1) *Arrangement.*—Slightly irregular around styles.
(2) *Number.*—Average 140–150.
(3) *Length.*—Average 8 to 10 mm from base.
(4) *Filaments.*—Color — Close to 48C.
(5) *Anthers.*—Color — Close to 26B.
(6) *Pollen.*—Close to 15A.

B. Pistil:
(1) *Styles.*—Length: 10–18 mm crossection extending from ovary wall; number: 130–140; color; near to 150D; heavily coated with white hairs.
(2) *Stigma.*—Color — Close to 20C.
(3) *Ovary.*—Shape — oblong; center crossection at sepal base: 8–9 mm.

C. Hips: Does not set seed.

Plant—as grown on Dr. Huey understock

A. Form: Upright.
B. Growth: Vigorous; Height: average 1–1½ m; Diameter: average 80 cm.
C. Rapid basal break development: Length of basil break to cluster branching: average 70–90 cm; cluster branching to bud tip: average 30–40 cm.
D. Foliage: Compound of 3 to 5 leaflets on cluster stem; 5 to 7 leaflets on main canes below cluster.
(1) *Size of mature 7 leaflet.*—Tip of leaflet to stipule base 18–19 cm.
(2) *Quantity.*—Stems well covered.
(3) *Color.*—New foliage upper side close to 146A, slight gloss; underside near 146B, matte finish. Old foliage upper side near to 147A, slight gloss; under side near to 148A, matte finish.
(4) *Shape.*—Oval with center pointed.
(5) *Texture.*—Very firm, very leathery.
(6) *Edge.*—Serration on outer edge. Average 3–4 points per 1 cm, with ½–1 mm peak.
(7) *Rachis.*—Glandular hair on upper side, none on lower side; few prickles on lower side 1–2 mm length, hooked, 3–4 cm spacing.
(8) *Stipules.*—Length 31–34 mm; auricle 4–6 mm. Edge of stipule to tip of auricle with few glandular hairs.

E. Resistance to disease: Powdery mildew, rust and black-spot — Good.
F. Wood:
*New wood.*—Color close to 148B.
*Old wood.*—Color close to 167B. Bark — smooth.
G. Thorns on mature wood:
*Size.*—6–12 mm.
*Number per 10 cm.*—Mature wood: 22–26 thorns.
*Shape.*—Downward curvature.
*Color.*—Early stage close to 182A; slight shading of 146D.
H. Winter hardiness: Good.

I claim:

1. A new and distinct rose cultivar of the hybrid tea class, substantially as herein shown and described.

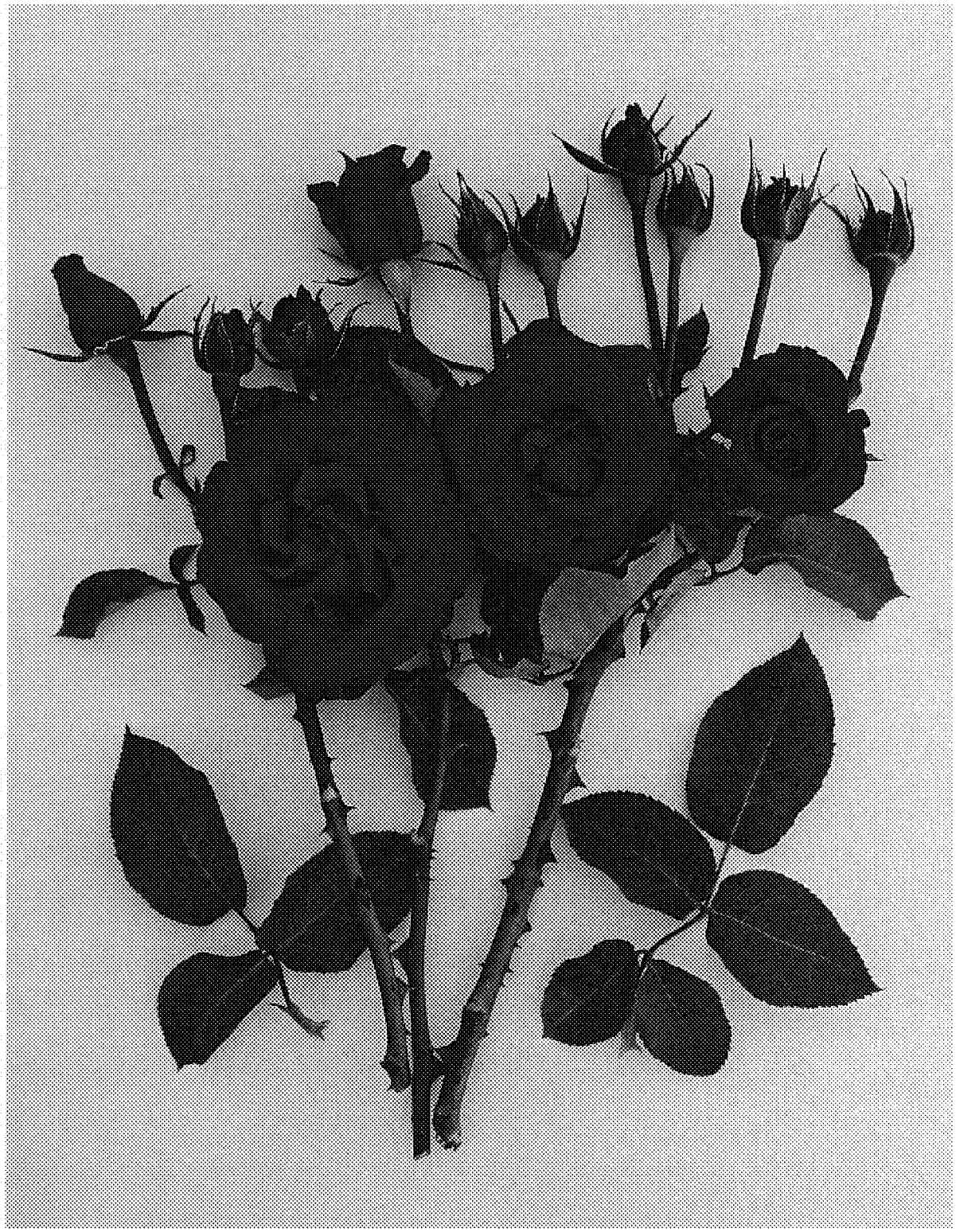

* * * * *